(12) United States Patent
Yoon et al.

(10) Patent No.: US 12,423,838 B2
(45) Date of Patent: Sep. 23, 2025

(54) MEDICAL IMAGE REGISTRATION METHOD AND APPARATUS

(71) Applicant: MEDICALIP CO., LTD., Gangwon-do (KR)

(72) Inventors: Soon Ho Yoon, Seoul (KR); Hyuk Hee Lee, Seoul (KR); Sang Joon Park, Seoul (KR)

(73) Assignee: MEDICALIP CO., LTD. (KR)

( * ) Notice: Subject to any disclaimer, the term of this patent is extended or adjusted under 35 U.S.C. 154(b) by 491 days.

(21) Appl. No.: 17/836,948

(22) Filed: Jun. 9, 2022

(65) Prior Publication Data

US 2022/0398752 A1    Dec. 15, 2022

(30) Foreign Application Priority Data

Jun. 10, 2021  (KR) .................. 10-2021-0075641

(51) Int. Cl.
*G06T 7/30* (2017.01)
*A61B 6/00* (2006.01)
(Continued)

(52) U.S. Cl.
CPC ............... *G06T 7/30* (2017.01); *A61B 6/032* (2013.01); *A61B 6/5235* (2013.01);
(Continued)

(58) Field of Classification Search
CPC . G06T 7/30; G06T 7/0012; G06T 7/11; G06T 2207/10081; G06T 2207/10116;
(Continued)

(56) References Cited

U.S. PATENT DOCUMENTS

2006/0291710 A1*  12/2006  Wang ................. G06T 15/08
                                                     382/154
2008/0037843 A1*   2/2008  Fu .......................... G06T 7/38
                                                     382/128
(Continued)

FOREIGN PATENT DOCUMENTS

CN    111402305 B  *  9/2020  ............ G06T 7/30
JP    2013-071016 A     4/2013
(Continued)

OTHER PUBLICATIONS

Evaluation of robot-based registration for subtraction radiography (Year: 1999).*

(Continued)

*Primary Examiner* — David Ometz
(74) *Attorney, Agent, or Firm* — Klarquist Sparkman, LLP

(57) ABSTRACT

A medical image registration method and apparatus are provided. The medical image registration apparatus generates a two-dimensional rigid image obtained by two-dimensionally projecting rigid tissue segmented from a three-dimensional medical image, generates a two-dimensional soft image obtained by two-dimensionally projecting soft tissue segmented from the three-dimensional medical image, registers a two-dimensional medical image with the two-dimensional rigid image, and registers the two-dimensional medical image with the two-dimensional soft image.

6 Claims, 11 Drawing Sheets

(51) Int. Cl.
*A61B 6/03* (2006.01)
*G06T 7/00* (2017.01)
*G06T 7/11* (2017.01)
*G16H 30/40* (2018.01)

(52) U.S. Cl.
CPC .............. *G06T 7/0012* (2013.01); *G06T 7/11* (2017.01); *G16H 30/40* (2018.01); *G06T 2207/10081* (2013.01); *G06T 2207/10116* (2013.01); *G06T 2207/30096* (2013.01)

(58) Field of Classification Search
CPC .......... G06T 2207/30096; A61B 6/032; A61B 6/5235; G16H 30/40
See application file for complete search history.

(56) References Cited

U.S. PATENT DOCUMENTS

| | | | | |
|---|---|---|---|---|
| 2014/0153797 | A1* | 6/2014 | Wan | G06T 7/38 382/128 |
| 2018/0150960 | A1* | 5/2018 | Derda | A61B 6/12 |
| 2020/0184639 | A1* | 6/2020 | Park | G06T 11/003 |

FOREIGN PATENT DOCUMENTS

| | | |
|---|---|---|
| KR | 10-2017-0086929 | 7/2017 |
| KR | 10-2018-0058071 | 5/2018 |
| KR | 10-2018-0099039 | 9/2018 |

OTHER PUBLICATIONS

Haas et al., "Automatic segmentation of thoracic and pelvic CT images for radiotherapy planning using implicit anatomic knowledge and organ-specific segmentation strategies," *Physics in Medicine & Biology* 53(6): 1751-1771, Mar. 2008.

Li et al., High-resolution chest x-ray bone suppression using unpaired CT structural *IEEE Transactions on Medical Imaging* 39(10): 3053-3063, Apr. 2020.

Mani V R S et al: "Survey of medical image registration," *Journal of Biomedical Engineering and Technology* 1(2): 8-25, Jan. 2013.

Xu et al., "Single-view 2D/3D registation for X-ray guided bronchoscopy." In 2010 *IEEE International Symposium on Biomedical Imaging: From Nano to Macro*, pp. 233-236. IEEE, Apr. 2010.

* cited by examiner

MEDICAL IMAGE REGISTRATION METHOD AND APPARATUS

ACKNOWLEDGMENT OF GOVERNMENT SUPPORT

This study is a research conducted with the support of the Korea Medical Device Development Fund funded by the government (Ministry of Science and Technology Information and Communication, Ministry of Trade, Industry and Energy, Ministry of Health and Welfare, and Ministry of Food and Drug Safety) (task identification number: 202012E08).

CROSS REFERENCE TO RELATED APPLICATION

This application is based on and claims priority under 35 U.S.C. § 119 to Korean Patent Application No. 10-2021-0075641, filed on Jun. 10, 2021, in the Korean Intellectual Property Office, the disclosure of which is incorporated by reference herein in its entirety.

FIELD

One or more embodiments relate to a medical image registration method and an apparatus therefor, and more particularly, to a method of registering a two-dimensional medical image, such as a radiographic image, and a three-dimensional medical image, such as a computed tomography (CT) image, and an apparatus therefor.

DESCRIPTION OF RELATED ART

A radiographic image (X-ray image), a computed tomography (CT) image, and a magnetic resonance imaging (MRI) image are used for lesion diagnosis. A radiographic image is a two-dimensional image, which is easy to take and inexpensive, but it is difficult to identify the detailed structure of the inside of the human body from the two-dimensional image. On the other hand, a CT image or an MRI image has the advantage of identifying the cross-sectional structure of the inside of the human body, but has disadvantages in that it takes a long of time and is expensive to take the CT or MRI image. A radiographic image is an image of a two-dimensional coordinate system and a CT image is an image of a three-dimensional coordinate system, and thus, it is difficult to register these two images. In addition, when a radiographic image and a CT image of the same part of the human body (for example, the chest) are captured, there is a certain difference between the radiographic image and the CT image due to the respiration or motion of a subject, and thus, the accuracy of registering the two images is low.

SUMMARY

One or more embodiments include a method and apparatus for segmenting a two-dimensional medical image and a three-dimensional medical image into rigid tissue and soft tissue and registering the same.

Additional aspects will be set forth in part in the description which follows and, in part, will be apparent from the description, or may be learned by practice of the presented embodiments of the disclosure.

According to one or more embodiments, a medical image registration method, performed by a medical image registration apparatus, includes: generating a two-dimensional rigid image obtained by two-dimensionally projecting rigid tissue segmented from a three-dimensional medical image; generating a two-dimensional soft image obtained by two-dimensionally projecting the three-dimensional medical image or a two-dimensional soft image obtained by two-dimensionally projecting soft tissue segmented from the three-dimensional medical image; registering a two-dimensional medical image with the two-dimensional rigid image; and registering the two-dimensional medical image with the two-dimensional soft image.

According to one or more embodiments, a medical image registration apparatus includes: a rigid image generator configured to generate a two-dimensional rigid image obtained by two-dimensionally projecting rigid tissue segmented from a three-dimensional medical image; a soft image generator configured to generate a two-dimensional soft image obtained by two-dimensionally projecting the three-dimensional medical image or a two-dimensional soft image obtained by two-dimensionally projecting soft tissue segmented from the three-dimensional medical image; a rigid registration unit configured to register a two-dimensional medical image with the two-dimensional rigid image; and a soft registration unit configured to register the two-dimensional medical image with the two-dimensional soft image.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
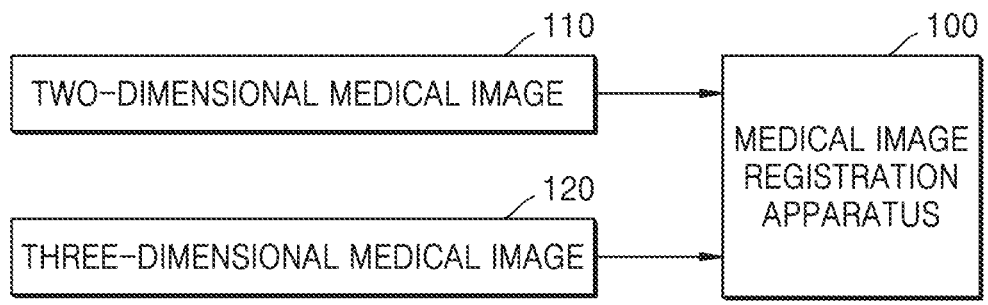
FIG. 1 illustrates a configuration of an example of a medical image registration apparatus according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a medical image registration method and apparatus according to an embodiment of the present disclosure will be described in detail with reference to the attached drawings.

FIG. 1 illustrates a configuration of an example of a medical image registration apparatus according to an embodiment of the present disclosure.

Referring to FIG. 1, upon receiving a two-dimensional medical image 110 and a three-dimensional medical image 120, a medical image registration apparatus 100 registers the two images. Here, registration refers to making the two images, which are taken separately, appear in one coordinate system.

The two-dimensional medical image 110 refers to an image composed of pixels in a two-dimensional coordinate system, and the three-dimensional medical image 120 refers to an image composed of voxels in a three-dimensional coordinate system. In the present embodiment, for convenience of description, a radiographic image is used as an example of the two-dimensional medical image 110 and a computed tomography (CT) image is used as an example of the three-dimensional medical image 120, but the two-dimensional medical image 110 and the three-dimensional medical image 120 are not limited thereto and may include other various types of images.

In an embodiment, the two-dimensional medical image 110 or the three-dimensional medical image 120 may be data stored according to the Digital Imaging and Communications in Medicine (DICOM) standard. In addition, the two-dimensional medical image 110 or the three-dimensional medical image 120 may be stored in other various types of image storage formats. In another embodiment, the two-dimensional medical image 110 or the three-dimensional medical image 120 may be stored in various systems or databases including a Picture Archiving and Communication System (PACS). For example, the medical image registration apparatus 100 may read the two-dimensional medical image 110 and the three-dimensional medical image 120 stored in the PACS, register the two images, and store a result of the registration in the PACS.

Figure 2:
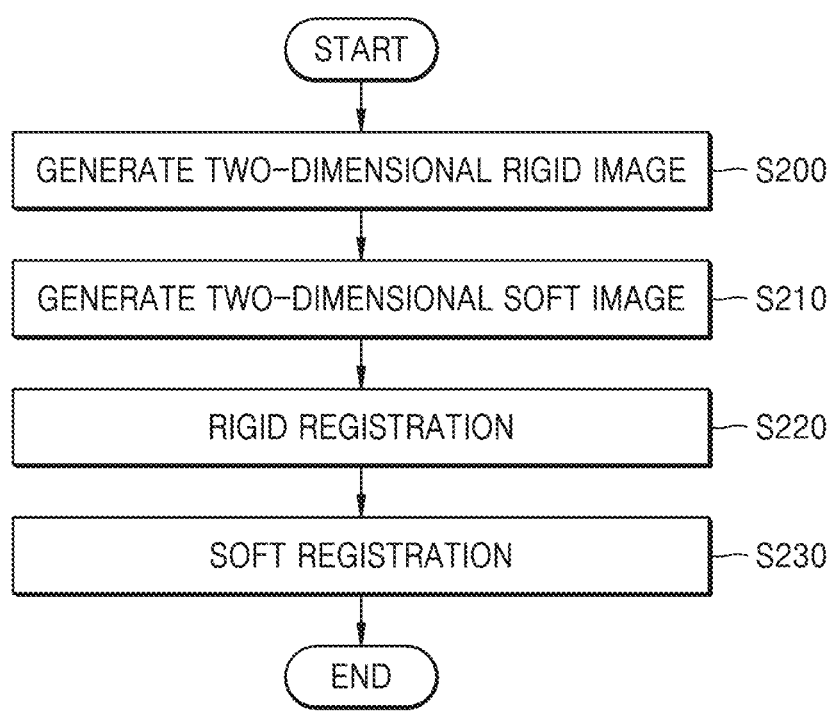
FIG. 2 is a flowchart of an example of a medical image registration method according to an embodiment of the present disclosure.

FIG. 2 is a flowchart of an example of a medical image registration method according to an embodiment of the present disclosure.

Referring to FIG. 2, the medical image registration apparatus 100 (hereinafter, referred to as 'apparatus') generates a two-dimensional rigid image obtained by two-dimensionally projecting rigid tissue segmented from a three-dimensional medical image (e.g., a CT image of the chest) in operation 5200. The rigid tissue refers to a hard part of the human body, and may be, for example, bone. When the rigid tissue is bone, a two-dimensional rigid image is a two-dimensional image of a bone region.

Various methods may be used to segment rigid tissue from a three-dimensional medical image to generate a two-dimensional rigid image. In an embodiment, the apparatus 100 may segment a bone region, which is rigid tissue, by using the feature that each human tissue (bone, organ, muscle, fat, etc.) has different voxel brightness values (HU, Hounsfield units) from each other in a three-dimensional medical image. For example, a three-dimensional bone region may be extracted by connecting voxels having brightness values corresponding to bone. Moreover, various methods according to the related art, of segmenting each human tissue from a three-dimensional medical image, such as segmenting rigid tissue by using an artificial intelligence model for segmenting human tissue, may be applied to the present embodiment, and the rigid tissue segmentation method is not limited to a specific method.

The apparatus 100 generates a two-dimensional soft image obtained by two-dimensionally projecting a three-dimensional medical image and/or a two-dimensional soft image obtained by two-dimensionally projecting soft tissue segmented from a three-dimensional medical image in operation 5210. In other words, the two-dimensional soft image may be an image generated using a three-dimensional medical image as it is or an image generated using a soft image segmented from a three-dimensional medical image. In another embodiment, a two-dimensional soft image obtained from a three-dimensional medical image and a two-dimensional soft image obtained from soft tissue segmented from a three-dimensional medical image may be used together.

Various segmentation algorithms may be used to segment soft tissue from a three-dimensional medical image. Here, the soft tissue may be a tissue, the movement of which is different from that of rigid tissue, according to respiration or motion of a subject. For example, when the soft tissue is the lung, the apparatus 100 may segment a three-dimensional lung region from a three-dimensional medical image, based on a voxel brightness value of the lung. Examples of a human tissue segmentation method are: Korean Patent Registration No. 10-1482247 titled "Airway Segmentation Method and Apparatus therefor", Korean Patent Registration No. 10-1514003 titled "Lunglobe Extraction Method and Apparatus", and Korean Patent Registration No. 10-2018-0098984 titled "Method of Separating Region from Medical Image and Apparatus therefor". Other various human tissue segmentation algorithms according to the related art may be applied to the present embodiment, and segmentation of rigid tissue and/or segmentation of soft tissue are not limited to any one algorithm.

When the chest is photographed, the positions of the bones and the lung may be different depending on the respiration or motion of a subject. In other words, when a state of the respiration (for example, inhalation or exhalation) or motion of the subject when capturing a two-dimensional medical image is different from the state of respiration or motion of the subject when capturing a three-dimensional medical image, the positional relationship between the bones and the lung in the two-dimensional medical image may be different from the positional relationship between the bones and the lung in the three-dimensional medical image. Thus, the apparatus 100 separately performs a registration process of rigid tissue and a registration process of soft tissue, as described below.

First, the apparatus 100 registers a two-dimensional medical image (e.g., a radiographic image of the chest) with the two-dimensional rigid image obtained above in operation S200. In the two-dimensional medical image, various human tissue, such as bones, organs, and muscles, are all superimposed on a two-dimensional plane. The apparatus 100 performs a registration process of adjusting a position, direction, size, etc. of the two-dimensional medical image and/or the two-dimensional rigid image such that a bone region in the two-dimensional rigid image and a bone region in the two-dimensional medical image match each other. Through the registration, a mapping relationship between each pixel of the two-dimensional medical image and each voxel of the three-dimensional medical image may be identified.

In an embodiment, the apparatus 100 may fix a two-dimensional medical image in a coordinate system and enlarge/reduce, rotate, or translate the two-dimensional rigid image in the coordinate system so that the bone regions of the two images match each other. For example, the apparatus 100 may superimpose a two-dimensional medical image and a two-dimensional rigid image in one coordinate system, and then register the two images by repeating a process of adjusting a size and a position of the two-dimensional rigid image such that a difference between a pixel brightness value of a bone region of the two-dimensional rigid image and a pixel brightness value of a region of the two-dimensional medical image corresponding to the bone region is minimized. Other various registration algorithms for registering two images, according to the related art, may be applied to the present embodiment.

Next, the apparatus 100 registers the two-dimensional medical image with the two-dimensional soft image in operation S230. For example, the apparatus 100 may fix the two-dimensional medical image in a coordinate system and register the two-dimensional medical image with the two-dimensional soft image by repeating a process of enlarging/reducing, translating, or rotating the two-dimensional soft image until an error (e.g., a root mean square (RMS) error, etc.) is minimized. Image registration is a well-known technique, and various registration algorithms according to the related art may be applied to the present embodiment.

The apparatus 100 may display the two-dimensional rigid image registered with the two-dimensional medical image in a superimposed manner or display the two-dimensional soft image registered with the two-dimensional medical image in a superimposed manner. As another example, based on a result of performing registration of a rigid image and a soft image, the apparatus 100 may display information about various tissue (e.g., bone, lung, lesion, etc.) identified from a three-dimensional medical image (e.g., size, volume, etc. of various tissue) on a two-dimensional medical image or provide the information to other devices along with the two-dimensional medical image. As another example, based on a registration result, the apparatus 100 may superimpose and display a lesion region inside and outside the rigid tissue or the soft tissue of the three-dimensional medical image on the two-dimensional medical image or provide the lesion region to another device along with the two-dimensional medical image.

While the process of performing registration of the soft image (S230) after registration of the rigid image (S220) is illustrated in the present embodiment, in another embodiment, the registration of the rigid image (S220) and the registration of the soft image (S230) may be performed in the reverse order or in parallel.

Figure 3:
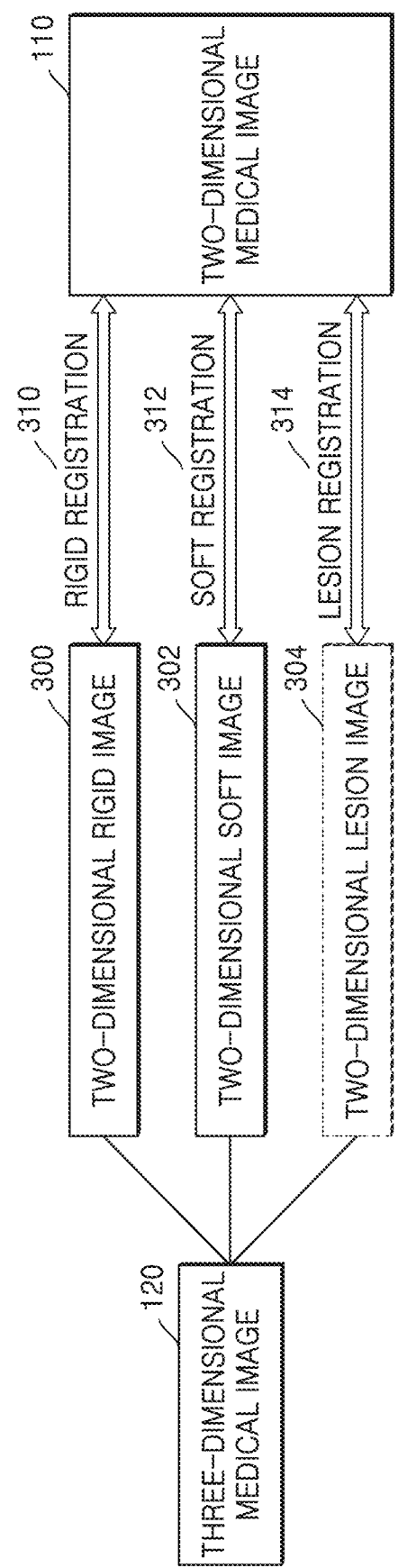
FIG. 3 illustrates types of registration according to an embodiment of the present disclosure.

FIG. 3 illustrates types of registration according to an embodiment of the present disclosure.

Referring to FIG. 3, the apparatus 100 performs rigid registration 310, soft registration 312, and lesion registration 314 on the three-dimensional medical image 120 and the two-dimensional medical image 110. According to an embodiment, the lesion registration 314 may be omitted. Hereinafter, an embodiment in which the lesion registration 314 is included is described.

The three-dimensional medical image 120 is a three-dimensional coordinate system image composed of voxel data, and the two-dimensional medical image 110 is a two-dimensional coordinate system image composed of pixel data, and thus, the apparatus 100 may reduce the dimension of the three-dimensional medical image 120 to two dimensions to generate a two-dimensional rigid image 300, a two-dimensional soft image 302, and a two-dimensional lesion image 304.

The two-dimensional rigid image 300 is generated by two-dimensionally projecting a three-dimensional rigid tissue region segmented from the three-dimensional medical image 120. For example, when bone is set as rigid tissue, the two-dimensional rigid image 300 is a two-dimensional image of the bone.

The two-dimensional soft image 302 is generated by two-dimensionally projecting a three-dimensional soft tissue region segmented from the three-dimensional medical image 120. For example, when the lung is set as soft tissue, the two-dimensional soft image 302 is a two-dimensional image of the lung. In another embodiment, the two-dimensional soft image 302 may be an image obtained by two-dimensionally projecting the three-dimensional medical image 120 as it is as a whole.

The two-dimensional lesion image 304 is an image generated by two-dimensionally projecting a lesion region segmented from the three-dimensional medical image 120. The lesion region may be various regions indicating a lesion, such as a tumor or inflammation. In the apparatus 100, various algorithms for segmenting a lesion region from the three-dimensional medical image 120, according to the related art, may be applied to the present embodiment. For example, various artificial intelligence models for recognizing lesions, according to the related art, may be applied to the present embodiment.

The rigid registration 310 is a process of registering the two-dimensional medical image 110 with the two-dimensional rigid image 300 by using various registration algorithms according to the related art, as described with reference to FIG. 2, and the soft registration 312 is a process of registering the two-dimensional medical image 110 with the two-dimensional soft image 302 by using various registration algorithms according to the related art.

In the case of the lesion registration 314, due to a small size of a lesion region, the accuracy of registration of the two-dimensional medical image 110 with the two-dimensional lesion image 304 may be low. Thus, in the present embodiment, the apparatus 100 does not directly apply a registration algorithm to the two-dimensional medical image 110 and the two-dimensional lesion image 304, but performs the lesion registration 314 of identically applying, to the two-dimensional lesion image 304, values for enlarging/reducing, translating or rotating the two-dimensional rigid image 300 or the two-dimensional soft image 302 for the rigid registration 310 or the soft registration 312. In other words, the lesion registration 314 is a process of applying, to the two-dimensional lesion image 304, values of enlargement/reduction, translation, or rotation, which are applied to the two-dimensional rigid image 300 or the two-dimensional soft image 302.

For example, when there is a lesion region in soft tissue, such as lung tissue, the apparatus 100 applies, to the two-dimensional lesion image 304, values for enlargement/reduction, translation, or rotation, which are applied to the two-dimensional soft image 302 during the soft registration process 312. As another example, when there is a lesion region in rigid tissue, such as bone tissue, the apparatus 100 applies, to the two-dimensional lesion image 304, values for enlargement/reduction, translation, or rotation, which are applied to the two-dimensional rigid image 300 during the rigid registration 310.

Figure 4:
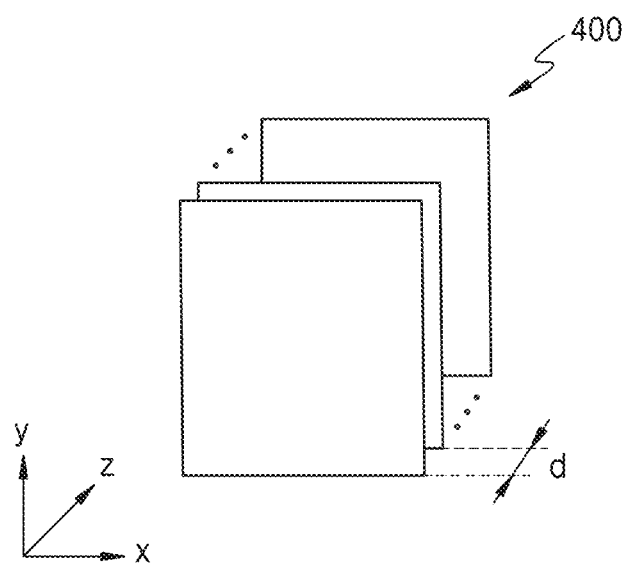
FIG. 4 illustrates an example of a three-dimensional medical image according to an embodiment of the present disclosure.

FIG. 4 illustrates an example of a three-dimensional medical image according to an embodiment of the present disclosure. Referring to FIG. 4, a three-dimensional medical image 400 includes a plurality of tomographic images. The plurality of tomographic images are composed of voxel data. That is, the three-dimensional medical image 400 is composed of a plurality of pieces of voxel data.

Figure 5:
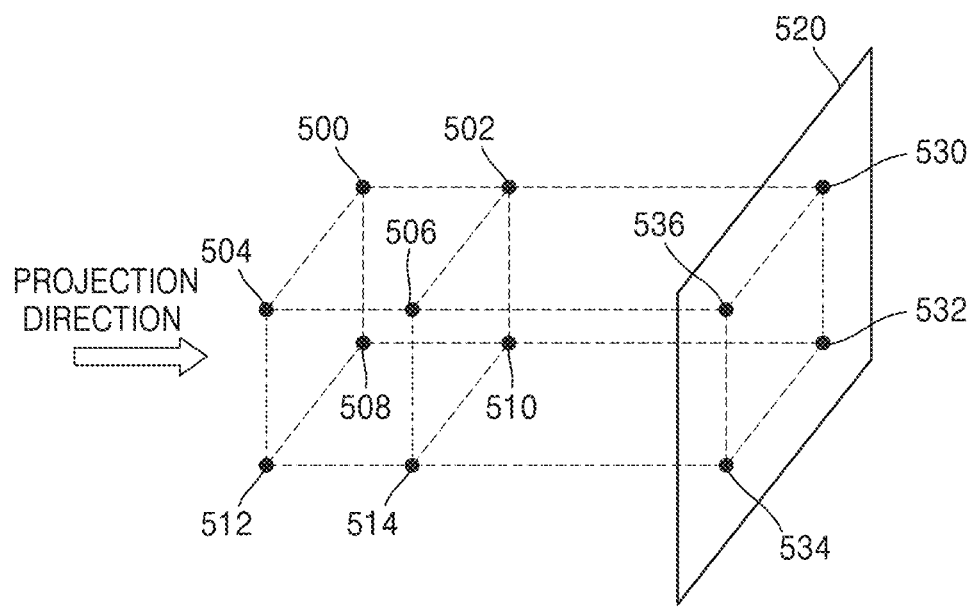
FIGS. 5 and 6 illustrate an example of a method of two-dimensionally projecting a three-dimensional medical image, according to an embodiment of the present disclosure.
Figure 6:
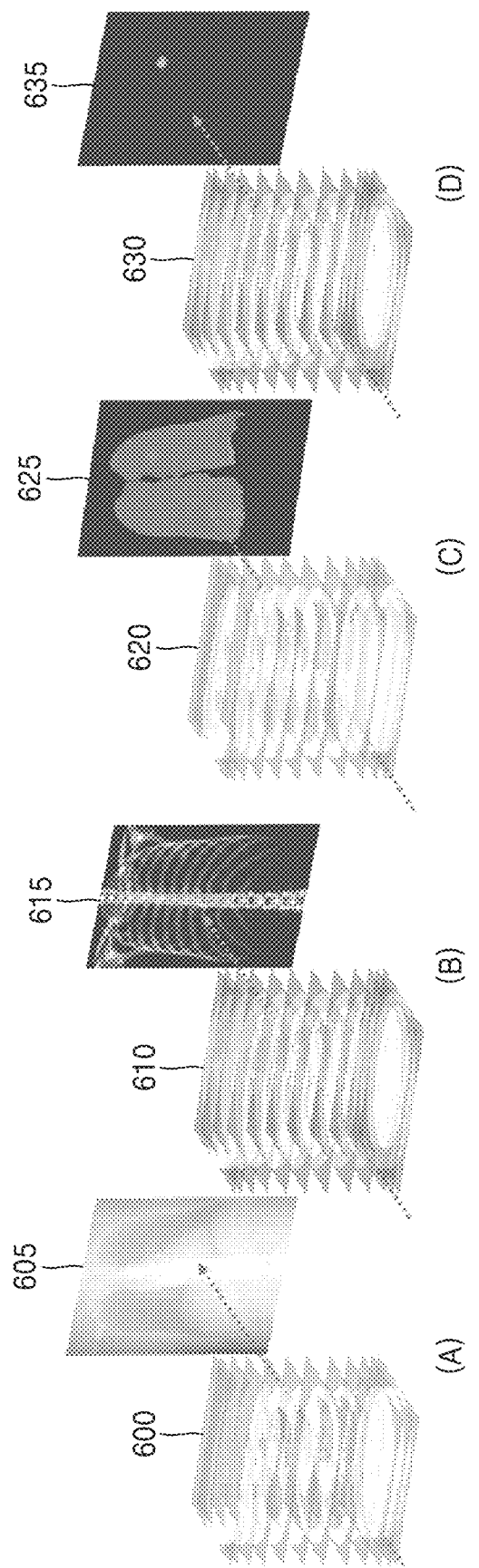

FIGS. 5 and 6 illustrate an example of a method of two-dimensionally projecting a three-dimensional medical image, according to an embodiment of the present disclosure.

Referring to FIG. 5, a three-dimensional medical image is composed of a plurality of voxels 500, 502, 504, 506, 508, 510, 512, and 514 respectively including brightness values as illustrated in FIG. 4. For convenience of description, only eight voxels 500, 502, 504, 506, 508, 510, 512, and 514 of a three-dimensional medical image are illustrated in the present embodiment. Here, the three-dimensional medical image may be a three-dimensional rigid tissue region or a three-dimensional soft tissue region, which is segmented from the three-dimensional medical image. However, for convenience of description, the regions will be described as a three-dimensional medical image below.

The apparatus 100 projects the three-dimensional medical image onto a virtual plane 520 in a certain direction in order to reduce the dimensionality of the three-dimensional medical image to two-dimensions. An image projected onto the virtual plane 520 is a two-dimensional image. The apparatus 100 generates a brightness value of the two-dimensional image by averaging brightness values of voxels superimposed in a projection direction.

For example, when a virtual imaging direction (i.e., a projection direction) is parallel to an X-axis, the apparatus 100 may average brightness values of the first voxel 500 and the second voxel 502 that are superimposed in the projection direction, and generate a brightness value of a first pixel 530 of the two-dimensional image projected onto the virtual plane 520. By using the above method, the apparatus 100 may generate a brightness value of a second pixel 536 by averaging brightness values of the third and fourth voxels 504 and 506, generate a brightness value of a third pixel 532 by averaging brightness values of the fifth and sixth voxels 508 and 510, and generate a brightness value of a third pixel 534 by averaging brightness values of the seventh and eighth voxels 512 and 514.

Referring to FIG. 6, a two-dimensional soft image 605 may be generated by two-dimensionally projecting a three-dimensional medical image 600 as it is (A), or a two-dimensional rigid image 615 may be generated by two-dimensionally projecting a region 610 of rigid tissue (e.g., bone) segmented from the three-dimensional medical image 600 (B), or a two-dimensional soft image 625 may be generated by two-dimensionally projecting a region 620 of soft tissue (e.g., a lung) segmented from the three-dimensional medical image 600, or a two-dimensional lesion image 635 may be generated by two-dimensionally projecting a lesion region 630 segmented from the three-dimensional medical image 600 (D).

Figure 7:
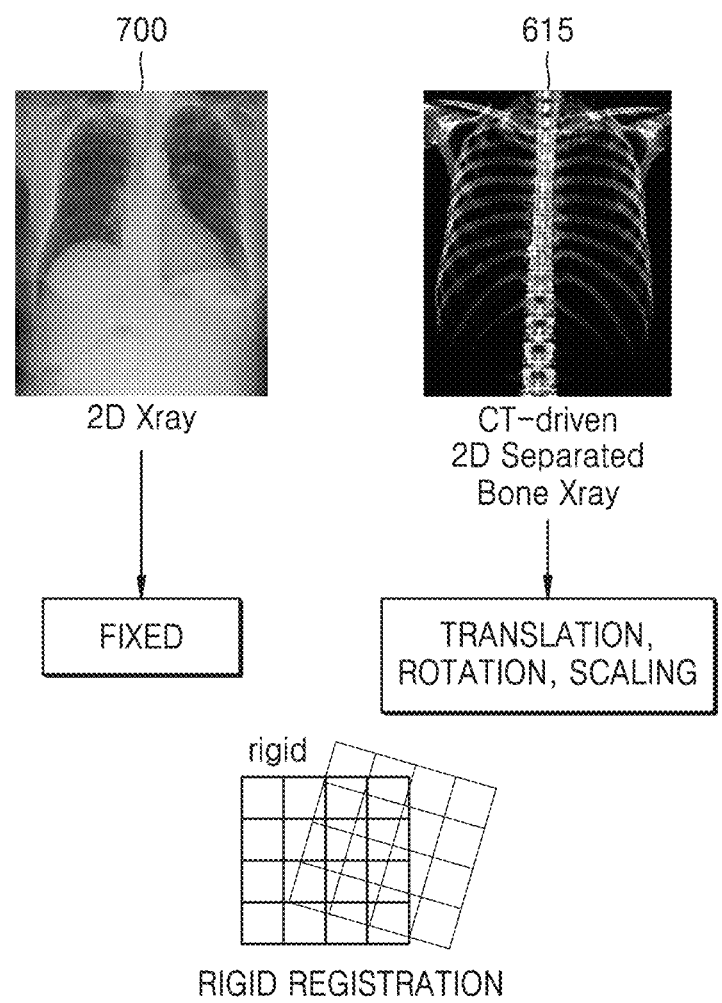
FIG. 7 illustrates an example of rigid registration according to an embodiment of the present disclosure.

FIG. 7 illustrates an example of rigid registration according to an embodiment of the present disclosure.

Referring to FIGS. 6 and 7 together, the apparatus 100 may fix a two-dimensional medical image 700 (e.g., a radiographic image), and register the two-dimensional medical image 700 with the two-dimensional rigid image 615 by translating, rotating, or scaling the two-dimensional rigid image 615.

Figure 8:
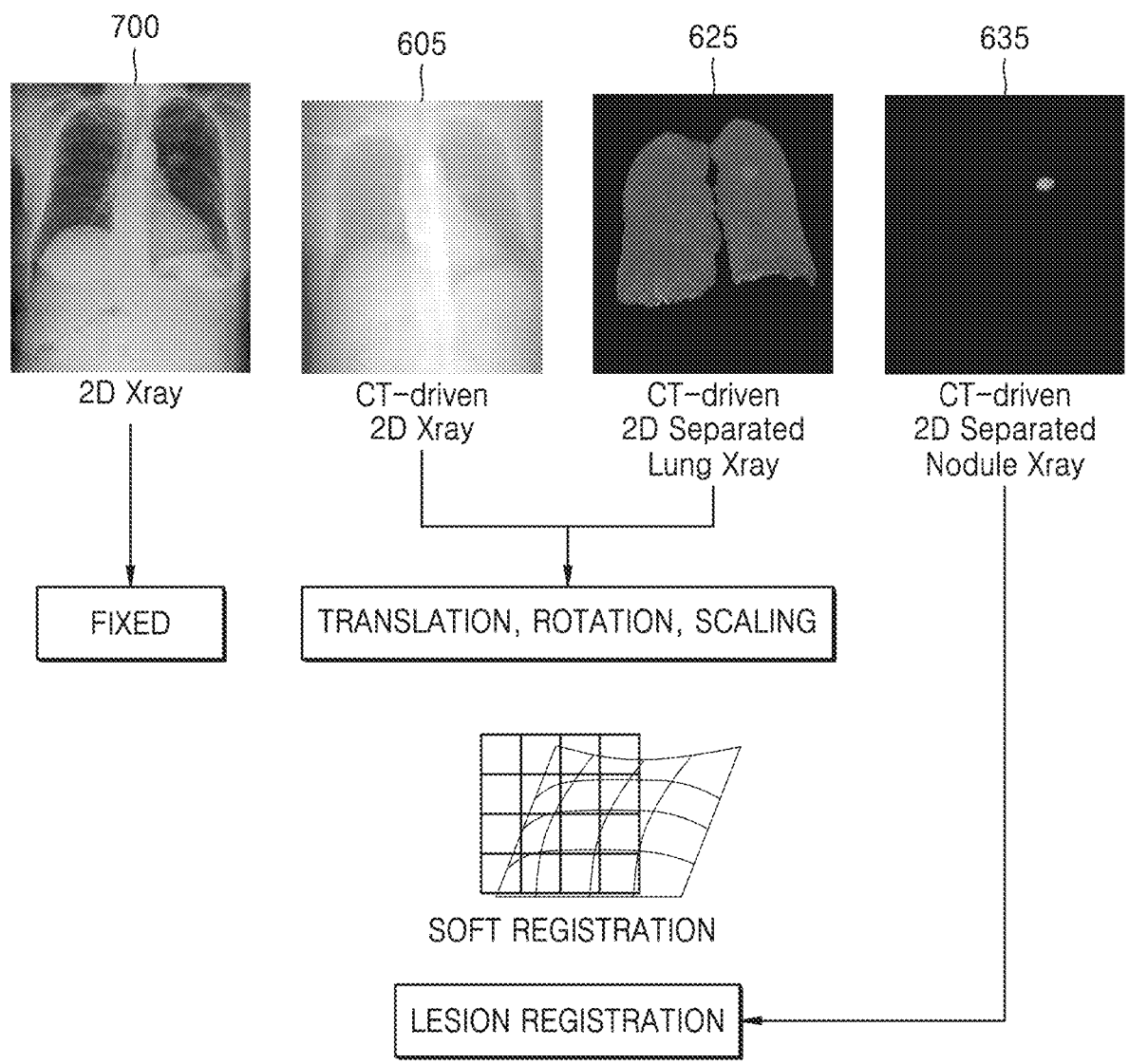
FIG. 8 illustrates an example of soft registration according to an embodiment of the present disclosure.

FIG. 8 illustrates an example of soft registration according to an embodiment of the present disclosure.

Referring to FIGS. 6 and 8 together, the apparatus 100 may fix the two-dimensional medical image 700 (e.g., a radiographic image), and register the two-dimensional medical image 700 with the two-dimensional soft image 605 or 625 by translating, rotating, or scaling the two-dimensional soft image 605 or 625.

The apparatus 100 may also register the two-dimensional lesion image 635 obtained by two-dimensionally projecting a lesion region (e.g., a tumor, inflammation, etc.) segmented from a three-dimensional medical image, with the two-dimensional medical image 700. While the present embodiment shows an example in which there is a lesion region in soft tissue, the lesion region may also be in rigid tissue. The apparatus 100 does not perform a registration process by directly comparing the two-dimensional medical image 700 with the two-dimensional lesion image 635, but register the two-dimensional lesion image 635 by using a result of performing a process of registering the two-dimensional medical image 700 with the two-dimensional soft image 605 or 625. The above method is illustrated in FIG. 9.

Figure 9:
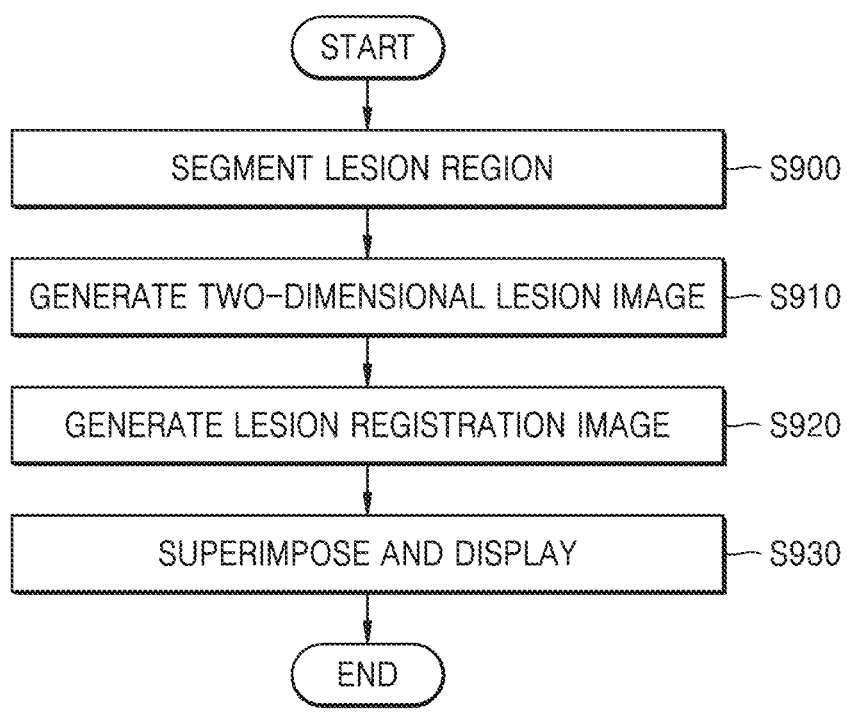
FIG. 9 is a flowchart of an example of lesion registration according to an embodiment of the present disclosure.

FIG. 9 is a flowchart of an example of a lesion registration method according to an embodiment of the present disclosure.

Referring to FIG. 9, the apparatus 100 segments a lesion region from a three-dimensional medical image in operation 5900. The apparatus 100 generates a two-dimensional lesion image by two-dimensionally projecting a three-dimensional lesion region segmented from the three-dimensional medical image, by using the projection method as illustrated in FIG. 5 in operation 5910.

The apparatus 100 generates a lesion registration image by applying, to the two-dimensional lesion region, values for translation, rotation, or scaling of a two-dimensional rigid image or a two-dimensional soft image, identified from a process of rigid registration between a two-dimensional medical image and the two-dimensional rigid image or a process of soft registration between the two-dimensional medical image and the two-dimensional soft image in operation 5920.

For example, when there is a lesion region in rigid tissue, for rigid registration, the apparatus 100 performs lesion registration by using the values for translation, rotation, and scaling of the two-dimensional rigid image, which are applied to the two-dimensional rigid image, and when there is a lesion region in soft tissue, the apparatus 100 performs, for soft registration, lesion registration by using the values for translation, rotation, and scaling of the two-dimensional soft image, which are applied to the two-dimensional soft image.

The apparatus 100 may superimpose and display the lesion registration image on the two-dimensional medical image in operation 5930. An example of superimposing the lesion registration image on the two-dimensional medical image is shown in FIG. 10.

Figure 10:
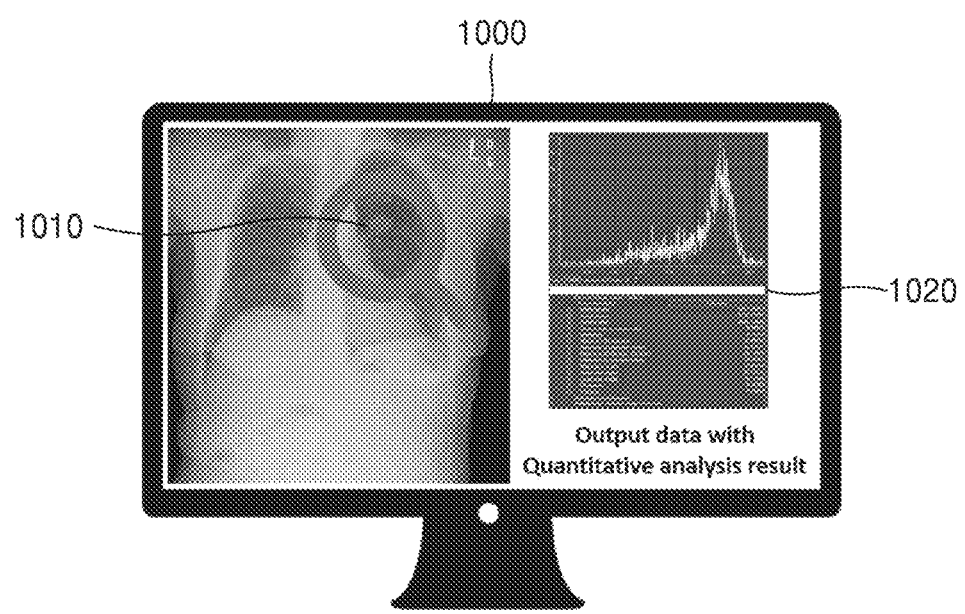
FIG. 10 illustrates lesion of a three-dimensional medical image superimposed and displayed on a two-dimensional medical image through a registration process according to an embodiment of the present disclosure.

FIG. 10 illustrates lesion of a three-dimensional medical image, superimposed and displayed on a two-dimensional medical image through a registration process according to an embodiment of the present disclosure.

Referring to FIG. 10, the apparatus 100 may detect and display a location of a lesion region 1010 in a two-dimensional medical image 1000. For example, the apparatus 100 may register a two-dimensional lesion image obtained from a three-dimensional medical image, by the method of FIG. 9, with a two-dimensional medical image, and then display a position of the registered two-dimensional lesion image on the two-dimensional medical image. In addition, the apparatus 100 may display various types of information 1020 (e.g., size and volume of a lesion) identified from the three-dimensional medical image together with the two-dimensional medical image 1000.

Figure 11:
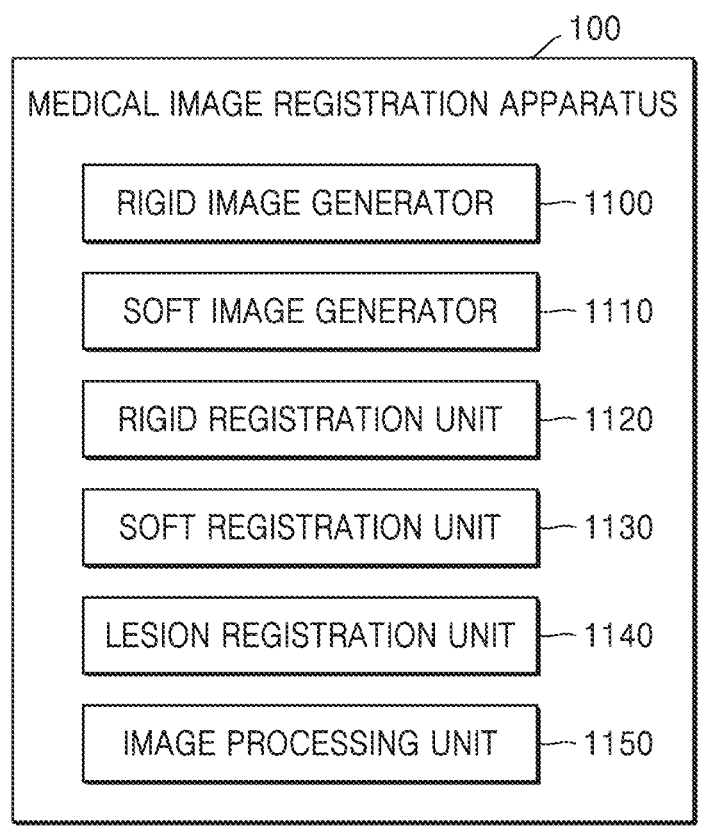
FIG. 11 illustrates a configuration of an example of a medical image registration apparatus according to an embodiment of the present disclosure.

FIG. 11 illustrates a configuration of an example of a medical image registration apparatus according to an embodiment of the present disclosure.

Referring to FIG. 11, the medical image registration apparatus 100 (hereinafter, "apparatus") may include a rigid image generator 1100, a soft image generator 1110, a rigid registration unit 1120, a soft registration unit 1130, a lesion registration unit 1140, and an image processing unit 1150. The apparatus 100 may be implemented by a computing device including a memory and a processor, and each component may be mounted in the memory and executed by the processor. In addition, some of the components of the present embodiment (e.g., the lesion registration unit 1140 and the image processing unit 1150) may be omitted.

The rigid image generator 1100 generates a two-dimensional rigid image obtained by two-dimensionally projecting rigid tissue segmented from a three-dimensional medical image. For example, the rigid image generator 1100 may segment a bone region, which is rigid tissue, from a three-dimensional medical image, and then generate a two-dimensional rigid image obtained by two-dimensionally projecting a three-dimensional bone region.

The soft image generator 1110 generates a two-dimensional soft image obtained by two-dimensionally projecting a three-dimensional medical image or a two-dimensional soft image obtained by two-dimensionally projecting soft tissue segmented from a three-dimensional medical image. For example, the soft image generator 1110 may segment a lung region, which is soft tissue, from a three-dimensional medical image, and then generate a two-dimensional soft image obtained by two-dimensionally projecting a three-dimensional lung region.

The rigid registration unit 1120 registers a two-dimensional medical image with a two-dimensional rigid image. For example, the rigid registration unit 1120 may fix a two-dimensional medical image, and register the two-dimensional medical image with a two-dimensional rigid image by translating, rotating, or scaling the two-dimensional rigid image.

The soft registration unit 1130 registers a two-dimensional medical image with a two-dimensional soft image. For example, the soft registration unit 1130 may fix a two-dimensional medical image, and register the two-dimensional medical image with a two-dimensional soft image by translating, rotating, or scaling the two-dimensional soft image. An image registration algorithm is well known, and various registration algorithms according to the related art may be used in rigid registration and/or soft registration.

The lesion registration unit 1140 registers a two-dimensional medical image with a two-dimensional lesion image. However, the lesion registration unit 1140 registers a two-dimensional lesion image with a two-dimensional medical image by using a registration result of the rigid registration unit 1120 or the soft registration unit 1130, instead of using a registration algorithm according to the related art. For example, when there is a lesion in soft tissue, the lesion registration unit 1140 may generate a lesion registration image by applying, to a two-dimensional lesion image, values for translating, rotating, or scaling the two-dimensional soft image by the soft registration unit 1130 for registration of the two-dimensional soft image.

The image processing unit 1150 may generate an image obtained by excluding rigid or soft tissue from a two-dimensional medical image. For example, when the two-dimensional medical image and the two-dimensional rigid image are registered, the image processing unit 1150 may generate an image obtained by removing rigid tissue (e.g., bone) of the two-dimensional rigid image, from the two-dimensional medical image. The image processing unit 1150 may correct a pixel brightness of a rigid tissue region removed from the two-dimensional medical image to be the same as a pixel brightness of tissue around the bone. As another example, when a two-dimensional medical image and a two-dimensional soft image are registered, the image processing unit 1150 may generate an image obtained by removing a region corresponding to soft tissue of the two-dimensional soft image, from the two-dimensional medical image.

The present disclosure may also be implemented as computer-readable code on a computer-readable recording medium. The computer-readable recording medium includes all types of recording devices in which data readable by a computer system is stored. Examples of computer-readable recording media include read only memory (ROM), random access memory (RAM), a compact disk ROM (CD-ROM), a solid state disk (SSD), and optical data storage devices. In addition, the computer-readable recording medium is distributed in a network-connected computer system so that the computer-readable code can be stored and executed in a distributed manner.

According to an embodiment of the present disclosure, by segmenting rigid tissue and soft tissue, a two-dimensional medical image and a three-dimensional medical image may be registered. In addition, a two-dimensional medical image and a three-dimensional medical image, which differ from each other due to respiration or motion of a subject, may be accurately registered. As another embodiment, a location of a lesion may be accurately marked on a two-dimensional medical image by using a three-dimensional medical image.

While the present disclosure has been particularly shown and described with reference to embodiments thereof, it will be understood by those of ordinary skill in the art that various changes in form and details may be made therein without departing from the spirit and scope of the present disclosure as defined by the appended claims. Thus, the disclosed embodiments should be considered in a descriptive sense only and not for purposes of limitation. Therefore, the scope of the present disclosure is defined not by the detailed description of the present disclosure but by the appended claims, and all differences within the scope will be construed as being included in the present disclosure.

We claim:

1. A medical image registration method performed by a medical image registration apparatus, the method comprising:
   generating a two-dimensional rigid image obtained by two-dimensionally projecting rigid tissue segmented from a three-dimensional medical image;
   generating a two-dimensional soft image obtained by two-dimensionally projecting the three-dimensional medical image or a two-dimensional soft image obtained by two-dimensionally projecting soft tissue segmented from the three-dimensional medical image;
   registering a two-dimensional medical image with the two-dimensional rigid image;

registering the two-dimensional medical image with the two-dimensional soft image, and segmenting a lesion region from the three-dimensional medical image;

generating a two-dimensional lesion image obtained by two-dimensionally projecting the lesion region;

generating a lesion registration image by applying, to the two-dimensional lesion image, values for translating, rotating, or scaling previously applied to the two-dimensional soft image for registration between the two-dimensional medical image and the two-dimensional soft image; and superimposing and displaying the lesion registration image on the two-dimensional medical image.

2. The medical image registration method of claim 1, wherein the two-dimensional medical image comprises a radiographic image, and the three-dimensional medical image comprises a computed tomography (CT) image.

3. The medical image registration method of claim 1, further comprising, when the two-dimensional medical image is registered with the two-dimensional rigid image, generating an image obtained by removing rigid tissue from the two-dimensional medical image based on the registered two-dimensional rigid image.

4. A non-transitory computer-readable recording medium having recorded thereon a computer program for executing the method of claim 1.

5. A medical image registration apparatus comprising:

a rigid image generator configured to generate a two-dimensional rigid image obtained by two-dimensionally projecting rigid tissue segmented from a three-dimensional medical image;

a soft image generator configured to generate a two-dimensional soft image obtained by two-dimensionally projecting the three-dimensional medical image or a two-dimensional soft image obtained by two-dimensionally projecting soft tissue segmented from the three-dimensional medical image;

a rigid registration unit configured to register a two-dimensional medical image with the two-dimensional rigid image;

a soft registration unit configured to register the two-dimensional medical image with the two-dimensional soft image; and a lesion registration unit configured to generate a lesion registration image by generating a two-dimensional lesion image obtained by two-dimensionally projecting a lesion region segmented from the three-dimensional medical image, and applying, to the two-dimensional lesion image, values for translating, rotating, or scaling previously applied to the two-dimensional soft image for registration between the two-dimensional medical image and the two-dimensional soft image.

6. The medical image registration apparatus of claim 5, further comprising an image processing unit configured to, when the two-dimensional medical image is registered with the two-dimensional rigid image, generate an image obtained by removing rigid tissue from the two-dimensional medical image based on the registered two-dimensional rigid image.

* * * * *